(12) United States Patent
Springer et al.

(10) Patent No.: US 9,011,826 B2
(45) Date of Patent: Apr. 21, 2015

(54) COSMETIC AND DERMATOLOGICAL FORMULATIONS INCLUDING ISONONYL BENZOATE

(75) Inventors: Oliver Springer, Wesel (DE); Oliver Thum, Ratingen (DE); Jürgen Meyer, Essen (DE); Klaus Jenni, Essen (DE)

(73) Assignee: Evonik Degussa GmbH, Essen (DE)

( * ) Notice: Subject to any disclaimer, the term of this patent is extended or adjusted under 35 U.S.C. 154(b) by 1189 days.

(21) Appl. No.: 12/273,921

(22) Filed: Nov. 19, 2008

(65) Prior Publication Data

US 2009/0136437 A1 May 28, 2009

(30) Foreign Application Priority Data

Nov. 21, 2007 (DE) .................. 10 2007 055 483

(51) Int. Cl.
| | | |
|---|---|---|
| A61K 8/37 | (2006.01) | |
| A61K 31/235 | (2006.01) | |
| A61Q 17/04 | (2006.01) | |
| A61K 8/49 | (2006.01) | |
| A61Q 19/00 | (2006.01) | |

(52) U.S. Cl.
CPC .................. *A61K 8/37* (2013.01); *A61K 8/4966* (2013.01); *A61Q 17/04* (2013.01); *A61Q 19/00* (2013.01)

(58) Field of Classification Search
USPC .......................................... 424/59; 514/544
See application file for complete search history.

(56) References Cited

U.S. PATENT DOCUMENTS

| | | |
|---|---|---|
| 6,635,775 B1 | 10/2003 | Walele et al. |
| 7,074,419 B2 | 7/2006 | Dietz et al. |
| 2004/0015007 A1 | 1/2004 | Grass et al. |
| 2004/0258649 A1 | 12/2004 | Peggau et al. |
| 2005/0180931 A1* | 8/2005 | Oguchi et al. .................. 424/59 |
| 2005/0232877 A1 | 10/2005 | Schunicht et al. |
| 2006/0165627 A1 | 7/2006 | Allef et al. |
| 2006/0204468 A1 | 9/2006 | Allef et al. |
| 2007/0092470 A1 | 4/2007 | Allef et al. |
| 2007/0128143 A1 | 6/2007 | Gruning et al. |
| 2007/0178144 A1 | 8/2007 | Hameyer et al. |
| 2008/0004357 A1 | 1/2008 | Meyer et al. |
| 2008/0108709 A1 | 5/2008 | Meyer et al. |

FOREIGN PATENT DOCUMENTS

| | | |
|---|---|---|
| DE | 1 165 574 | 10/1964 |
| DE | 37 40 186 A1 | 1/1989 |
| DE | 39 38 140 A1 | 8/1991 |
| DE | 40 09 347 A1 | 9/1991 |
| DE | 42 38 081 A1 | 7/1993 |
| DE | 42 04 321 A1 | 8/1993 |
| DE | 42 29 707 A1 | 3/1994 |
| DE | 42 29 737 A1 | 3/1994 |
| DE | 43 09 372 A1 | 9/1994 |
| DE | 43 24 219 A1 | 1/1995 |
| DE | 198 55 934 A1 | 6/2000 |
| DE | 102 17 186 A1 | 11/2003 |
| DE | 10 2004 027 475 A1 | 6/2006 |
| EP | 0 666 732 B1 | 8/1995 |
| EP | 1 354 867 A2 | 10/2003 |
| EP | 1 550 429 A1 | 7/2005 |

OTHER PUBLICATIONS

Finkel, P., "Formulierung Kosmetischer Sonnenschutzmittel" SÖFW-Journal (1996) pp. 543-548, vol. 122.
U.S. Appl. No. 12/198,574, entitled, "Use of Ester-Modified Organopolysiloxanes for Producing Cosmetic or Pharmaceutical Compositions," filed Aug. 26, 2008, First Named Inventor: Oliver Thum.
U.S. Appl. No. 12/132,307, entitled, "Stable, Low Viscosity Cosmetic Compositions," filed Jun. 3, 2008, First Named Inventor: Klaus Jenni.

\* cited by examiner

*Primary Examiner* — Ernst V Arnold
*Assistant Examiner* — Hong Yu
(74) *Attorney, Agent, or Firm* — Scully, Scott, Murphy & Presser, P.C.

(57) ABSTRACT

A method for the preparation of a formulation including adding at least one substance of the general formula (I)

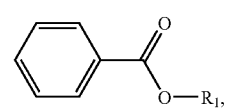

wherein $R_1$ is an unbranched or branched $C_9$-alkyl radical to at least one component selected from the group of an emollient, emulsifier, surfactant, thickener, viscosity regulator, stabilizer, UV light protection filter, antioxidant, hydrotropic agent, filler, film-forming agent, pearlescent additive, deodorant active compound, antiperspirant active compound, insect repellent, self-tanning agent, preservative, conditioning agent, perfume, dyestuff, biogenic active compound, care additive, super-oiling agent, and solvent.

29 Claims, No Drawings

COSMETIC AND DERMATOLOGICAL FORMULATIONS INCLUDING ISONONYL BENZOATE

FIELD OF THE INVENTION

The present invention relates to the use of isononyl benzoate for the preparation of a cosmetic, dermatological or pharmaceutical formulation. Isononyl benzoate is distinguished both in that it imparts good sensorial properties and by very good solution properties for active substances, in particular organic UV light protection filters.

BACKGROUND OF THE INVENTION

The consumer has a large number of requirements in the field of cosmetic emulsions for skin and hair care: Apart from the cleansing and care effects, which determine the intended use, value is placed on such different parameters as the highest possible dermatological tolerability, good re-oiling properties, elegant appearance, optimum sensorial impression and storage stability.

Formulations which are employed for cleansing and care of human skin and of hair as a rule comprise, in addition to a number of surface-active substances, oil substances and water. Oil substances/emollients which are employed are, for example, hydrocarbons, ester oils and plant and animal oils/fats/waxes. To meet the high requirements of the market with respect to sensorial properties and optimum dermatological tolerability, novel oil substances and emulsifier mixtures are continuously being developed and tested.

It is furthermore known that relatively large amounts of the ultraviolet content in natural and artificial light sources (e.g., UV-A 320-390 nm; UV-B 280-320 nm; UV-C 100 or 200-280 nm) lead to damage to the human skin.

UV-A radiation mainly has the effect of ageing the skin (thinning of the epidermis and degeneration of connective tissue, pigment disorders), while UV-B and UV-C lead to sunburn and skin cancer.

Leisure activities which have changed in recent years with longer periods in open air and, in particular, extensive sunbathing to achieve the "healthy tan" have, however, against the background of medical findings and the awareness of the lack of natural protection mechanisms of the skin by pigment formation and solar acclimatization by thickening of the horny layer, shifted the need for adequate protection against intensive UV radiation far into the foreground. It has been intensified significantly by the discussion of the decrease and thinning of the Antarctic ozone hole and the associated increase in the intensity of UV-A and UV-B radiation on the earth's surface.

This becomes clear from the increasing turnovers in recent years of products with high sun protection factors (SPF). These are mainly conventional sunscreen formulations (sun milk, sun oil) with the primary intended use of sunbathing, but increasingly also the so-called care products for the face, body and hair, such as day and night creams, conditioners, lotions, (hydro, lipo)gels, (lip)sticks and sprays, pharmaceutical formulations and to a small extent products of decorative cosmetics, which are predominantly commercially available in the form of oils and liquid, cream-like or ointment/paste-like W/O and O/W emulsions.

The light protection factor (LPF) or also SPF is a coefficient which expresses the ability of a product to prevent sunburn by the sun. Light protection with a factor of 60 therefore protects against the occurrence of sunburn for twice as long as a product with factor 30 and correspondingly three times as long as a product with factor 20.

These higher light protection factors are in most cases generated by an increase in the concentration of UV light protection filter substances in the formulation.

Since 1995 light protection factors have been measured by the same international standard (COLIPA), which allows comparison between the products of various manufacturers.

Given the frequent uses of these substances over large areas, it is not ruled out that the high-dosed filters (approx. 3 to 30 wt. % of the formulation) are applied to the skin in gram quantities. However, these amounts of filter substances must have been dissolved and incorporated into the formulation in a homogeneous and stable manner.

Oily components, which have a good dissolving power for the filter substances, are often used to dissolve these substances. Certain ester oils, inter alia, are thus also employed. Aliphatic benzoic acid esters are a class of compounds which can be employed. A typical representative of this class of compounds is the compound Tegosoft® TN(C12-C15 Alkyl Benzoate), which is employed frequently as a solvent for UV light protection filters.

Numerous compounds are known for protection against UV-B radiation, usually derivatives of 3-benzylidenecamphor, of 4-aminobenzoic acid, of cinnamic acid, of salicylic acid, of benzophenone and also of 2-phenylbenzimidazole.

It is also important to have filter substances available for the range between about 320 nm and about 400 nm, the so-called UV-A range, since rays in this range can also cause damage. It has been proved that UV-A radiation leads to damage to the elastic and collagen fibres of connective tissue, which makes the skin age prematurely, and that it is to be regarded as the cause of numerous phototoxic and photoallergic reactions. The harmful influence of UV-B radiation may be intensified by UV-A radiation.

4,4',4"-(1,3,5-Triazine-2,4,6-triyltriimino)-tris-benzoic acid tris(2-ethylhexyl ester), synonym: 2,4,6-tris-[anilino-(p-carbo-2'-ethyl-1'-hexyloxy)]-1,3,5-triazine, is a UV-B filter. This UV-B filter substance is marketed by BASF AG under the trade name UVINUL™ T 150 and is distinguished by good UV absorption properties.

The main disadvantage of this UV-B filter is the poor solubility in lipids. Known solvents for this UV-B filter can dissolve a maximum of approx. 15 wt. % of this filter, corresponding to about 1-1.5 wt. % of dissolved and therefore active UV light protection filter.

Isononyl benzoate is the ester of benzoic acid with isononanol. Isononyl benzoate is a compound which is known per se and employed as a fast-gelling, low-viscosity plasticizer for plastics (PVC, PAMA, PVB etc.) and adhesives and is marketed, inter alia, by Oxeno Olefinchemie GmbH under the trade name Vestinol® INB. Isononanol is listed, inter alia, under the Chemical Abstract Service (CAS) numbers 27458-94-2, 68515-81-1 or also 3452-97-9. Preparation is as a rule carried out by esterification of isononanol with benzoic acid, as described in DE 10217186. In this context, the esterification and treatment conditions can also be varied, as described, for example, in U.S. Pat. No. 6,635,775 for other benzoic acid esters.

SUMMARY OF THE INVENTION

The present invention provides an oil substance which, in addition to good sensorial properties, such as color, smell and sensation on the skin, also has a good solubility for active substances, in particular for organic UV light protection filters, such as, e.g., triazines, and preferably also for deodorant and antiperspirant active compounds.

Surprisingly it has been found by the applicants of the present application that isononyl benzoate meets these requirements.

The invention thus provides the use of isononyl benzoate for the preparation of a cosmetic, dermatological or pharmaceutical formulation. In particular, the present invention provides a method of fabricating one of a cosmetic formulation, a dermatological formulation and a pharmaceutical formulation that includes adding at least one substance of the general formula (I)

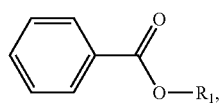
(I)

wherein $R_1$ is an unbranched or branched $C_9$-alkyl radical to at least one component selected from the group of an emollient, emulsifier, surfactant, thickener, viscosity regulator, stabilizer, UV light protection filter, antioxidant, hydrotropic agent (or polyol), filler, film-forming agent, pearlescent additive, deodorant active compound, antiperspirant active compound, insect repellent, self-tanning agent, preservative, conditioning agent, perfume, dyestuff, biogenic active compound, care additive, super-oiling agent, and solvent.

In one preferred embodiment of the invention, the at least one additional component is a UV light protection filter.

The invention also provides cosmetic, dermatological or pharmaceutical formulations comprising isononyl benzoate.

DETAILED DESCRIPTION OF THE INVENTION

The use according to the invention of isononyl benzoate and the formulations according to the invention comprising isononyl benzoate are described by way of example in the following, without the intention being to limit the invention to these embodiments given by way of example. Where ranges, general formulae or compound classes are mentioned in the following, these are intended to include not only the corresponding ranges or groups of compounds mentioned explicitly, but also all part ranges and part groups of compounds which can be obtained by removing individual values (ranges) or compounds. Where documents are cited in the context of the present description, it is intended that the content thereof in its entirety belongs to the disclosure content of the present invention. Where compounds such as e.g., organomodified polysiloxanes which can contain multiple various units are described in the context of the present invention, these units can occur in random distribution (statistical oligomer) or in an ordered manner (block oligomer) in these compounds. Data on the number of units in such compounds are to be understood as meaning the mean value, averaged over all the corresponding compounds. All the percentages (%) stated are percent by weight, unless stated otherwise.

In the following, isononyl benzoate is understood as meaning at least one substance of the general formula (I)

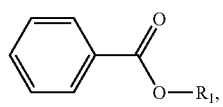
(I)

wherein $R_1$ can be an unbranched or branched $C_9$-alkyl radical, and isomer mixtures thereof.

According to the invention, at least one substance of the general formula (I) where $R_1$ is an unbranched or branched $C_9$-alkyl radical is used for the preparation of a cosmetic, dermatological or pharmaceutical formulation, in particular sunscreen preparations. However, individual isomers, for example the benzoic acid esters of n-nonanol, 2-methyloctanol, 2-ethylheptanol, 2-propylhexanol, 4-methyloctanol, 2,3-dimethylheptanol, 3-ethylheptanol, 2-propyl-3-methylpentanol, 2-ethyl-4-methyl-hexanol, 2,5-dimethylheptanol, 6-methyloctanol, 4,5-dimethylheptanol, 2,3,4-trimethylhexanol, 3-ethyl-4-methyl-hexanol and/or of 3,5,5-trimethylhexanol, can also be employed. Mixtures of the isomers are preferably used.

More preferably, one or more substances of the formula (I) are used, with the proviso that the nonyl alcohols obtained by hydrolysis of the substance(s) used contain less than 10 mol % of 3,5,5-trimethylhexanol.

The cosmetic, dermatological or pharmaceutical formulations and the care and cleansing compositions can comprise, e.g., at least one additional component selected from the group of
emollients,
emulsifiers and surfactants,
thickeners/viscosity regulators/stabilizers,
UV light protection filters,
antioxidants,
hydrotropic agents (or polyols),
solids and fillers,
film-forming agents,
pearlescent additives,
deodorant and antiperspirant active compounds,
insect repellents,
self-tanning agents,
preservatives,
conditioning agents,
perfumes,
dyestuffs,
biogenic active compounds,
care additives,
super-oiling agents,
solvents.

Emollients which can be employed in the invention are all cosmetic oils, in particular mono- or diesters of linear and/or branched mono- and/or dicarboxylic acids having 2 to 44 C atoms with linear and/or branched saturated or unsaturated alcohols having 1 to 22 C atoms. The esterification products of aliphatic difunctional alcohols having 2 to 36 C atoms with monofunctional aliphatic carboxylic acids having 1 to 22 C atoms can also be employed. Long-chain aryl acid esters, such as, e.g., esters of benzoic acid with linear and/or branched $C_6$-$C_{22}$-alcohols, or also benzoic acid isostearyl ester, benzoic acid butyloctyl ester or benzoic acid octyldodecyl ester, are furthermore suitable. Further monoesters which are suitable as emollients and oil components are e.g., the methyl esters and isopropyl esters of fatty acids having 12 to 22 C atoms, such as, for example, methyl laurate, methyl stearate, methyl oleate, methyl erucate, isopropyl myristate, isopropyl palmitate, isopropyl stearate, isopropyl oleate. Other suitable monoesters are, e.g., n-butyl stearate, n-hexyl laurate, n-decyl oleate, isooctyl stearate, isononyl palmitate, isononyl isononanoate, 2-ethylhexyl laurate, 2-ethylhexyl palmitate, 2-ethylhexyl stearate, 2-hexyldecyl stearate, 2-octyldodecyl palmitate, oleyl oleate, oleyl erucate, erucyl oleate and esters which are obtainable from technical-grade aliphatic alcohol cuts and technical-grade aliphatic carboxylic acid mixtures, e.g., esters of unsaturated fatty alcohols having 12 to 22 C atoms and saturated and unsaturated fatty acids having 12 to 22 C atoms, such as are accessible from animal and plant fats. However, naturally occurring monoester and wax ester mixtures such as are present, e.g., in jojoba oil or in sperm oil are also suitable. Suitable dicarboxylic acid esters are, e.g., di-n-butyl adipate, di-n-butyl sebacate, di-(2-ethylhexyl) adipate, di-(2-hexyldecyl) succinate, di-isotridecyl azelate. Suitable diol esters are, e.g., ethylene glycol dioleate, ethylene glycol di-isotridecanoate, propylene glycol di-(2-ethylhexanoate), butanediol di-isostearate, butanediol di-caprylate/caprate and neopentyl glycol di-caprylate. Further fatty acids which can be employed as emollients are, e.g., dicaprylyl carbonate, diethylhexyl carbonate. Longer-chain triglycerides, i.e., triple esters of glycerol with three acid molecules, at least one of which is longer-chain, can also be employed as emollients and oil components. There may be mentioned here by way of example fatty acid triglycerides; as such, for example, natural plant oils, e.g., olive oil, sunflower oil, soya oil, groundnut oil, rapeseed oil, almond oil, sesame oil, avocado oil, castor oil, cacao butter, and palm oil, but also the liquid contents of coconut oil or of palm kernel oil, as well as animal oils, such as, e.g., shark-fish liver oil, cod liver oil, whale oil, beef tallow and butter-fat waxes, such as beeswax, carnauba palm wax, spermaceti, lanolin and neat's foot oil, the liquid contents of beef tallow or also synthetic triglycerides of caprylic/capric acid mixtures, triglycerides from technical-grade oleic acid, triglycerides with isostearic acid, or from palmitic acid/oleic acid mixtures, can be employed as emollients and oil components. Hydrocarbons, including liquid paraffins and isoparaffins, can furthermore be employed. Examples of hydrocarbons which can be employed are paraffin oil, isohexadecane, polydecene, vaseline, paraffinum perliquidum, squalane, and ceresin. Linear or branched fatty alcohols, such as oleyl alcohol or octyldodecanol, and fatty alcohol ethers, such as dicaprylyl ether, can furthermore also be employed. Suitable silicone oils and waxes are, e.g., polydimethylsiloxanes, cyclomethylsiloxanes, and aryl- or alkyl- or alkoxy-substituted polymethylsiloxanes or cyclomethylsiloxanes. Further possible oil substances are, for example, Guerbet alcohols based on fatty alcohols having 6 to 18, preferably 8 to 10 carbon atoms, esters of linear $C_6$-$C_{22}$ fatty acids with linear $C_6$-$C_{22}$-fatty alcohols, esters of branched $C_6$-$C_{13}$-carboxylic acids with linear $C_6$-$C_{22}$-fatty alcohols, esters of linear $C_6$-$C_{22}$-fatty acids with branched $C_8$-$C_{18}$-alcohols, in particular 2-ethylhexanol or isononanol, esters of branched $C_6$-$C_{13}$-carboxylic acids with branched alcohols, in particular 2-ethylhexanol or isononanol, esters of linear and/or branched fatty acids with polyhydric alcohols (such as, e.g., propylene glycol, dimer diol or trimer triol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, plant oils, branched primary alcohols, substituted cyclohexanes, linear $C_6$-$C_{22}$-fatty alcohol carbonates, Guerbet carbonates, dialkyl ethers, ring-opening products of epoxidized fatty acid esters with polyols, silicone oils and/or aliphatic or naphthenic hydrocarbons.

Emulsifiers or surfactants which can be employed are nonionic, anionic, cationic or amphoteric surfactants.

Compounds from at least one of the following groups can be employed as nonionic emulsifiers or surfactants:

addition products of from 2 to 100 mol of ethylene oxide and/or 0 to 5 mol of propylene oxide on linear fatty alcohols having 8 to 22 C atoms, on fatty acids having 12 to 22 C atoms and on alkylphenols having 8 to 15 C atoms in the alkyl group, $C_{12/18}$-fatty acid mono- and diesters of addition products of from 1 to 100 mol of ethylene oxide on glycerol, glycerol mono- and diesters and sorbitan mono- and diesters of saturated and unsaturated fatty acids having 6 to 22 carbon atoms and ethylene oxide addition products thereof, alkyl mono- and oligoglycosides having 8 to 22 carbon atoms in the alkyl radical and ethylene oxide addition products thereof, addition products of from 2 to 200 mol of ethylene oxide on castor oil and/or hydrogenated castor oil, partial esters based on linear, branched, unsaturated or saturated $C_6$-$C_{22}$-fatty acids, -ricinoleic acid and 12-hydroxystearic acid and glycerol, polyglycerol, pentaerythritol, dipentaerythritol, sugar alcohols (e.g., sorbitol), alkyl glucosides (e.g., methyl glucoside, butyl glucoside, lauryl glucoside) and polyglucosides (e.g., cellulose), mono-, di- and trialkyl phosphates and mono-, di- and/or tri-PEG-alkyl phosphates and salts thereof, polysiloxane/polyether copolymers (Dimethicone Copolyols), such as, e.g., PEG/PPG-20/6 Dimethicone, PEG/PPG-20/20 Dimethicone, Bis-PEG/PPG-20/20 Dimethicone, PEG-12 or PEG-14 Dimethicone, PEG/PPG-14/4 or 4/12 or 20/20 or 18/18 or 17/18 or 15/15, polysiloxane/polyalkyl polyether copolymers and corresponding derivatives, such as, e.g., Lauryl or Cetyl Dimethicone Copolyols, in particular Cetyl PEG/PPG-10/1 Dimethicone (ABIL® EM 90 (Evonik Degussa)), mixed esters of pentaerythritol, fatty acids, citric acid and fatty alcohol according to DE 11 65 574 and/or mixed esters of fatty acids having 6 to 22 carbon atoms, methylglucose and polyols, such as, e.g., glycerol or polyglycerol.

citric acid esters, such as, e.g., Glyceryl Stearate Citrate, Glyceryl Oleate Citrate and Dilauryl Citrate.

Anionic emulsifiers or surfactants can contain groups which confer solubility in water, such as, e.g., a carboxylate, sulphate, sulphonate or phosphate group and a lipophilic radical. Anionic surfactants which are tolerated by skin are known in large numbers to the person skilled in the art and are commercially available. In this context, these can be alkyl sulphates or alkyl phosphates in the form of their alkali metal, ammonium or alkanolammonium salts, alkyl ether-sulphates, alkyl ether-carboxylates, acyl sarcosinates and sulphosuccinates and acyl glutamates in the form of their alkali metal or ammonium salts.

Cationic emulsifiers and surfactants can also be added. Quaternary ammonium compounds, in particular those provided with at least one linear and/or branched, saturated or unsaturated alkyl chain having 8 to 22 C atoms, can be employed as such, thus, for example, alkyltrimethylammonium halides, such as, e.g., cetyltrimethylammonium chloride or bromide or behenyltrimethylammonium chloride, but also dialkyldimethylammonium halides, such as, e.g., distearyldimethylammonium chloride.

Monoalkylamidoquats, such as, e.g., palmitamidopropyltrimethylammonium chloride, or corresponding dialkylamidoquats can furthermore be employed.

Readily biodegradable quaternary ester compounds, which can be quaternized fatty acid esters based on mono-, di- or triethanolamine, can furthermore be employed.

Alkylguanidinium salts can furthermore be admixed as cationic emulsifiers.

Typical examples of mild surfactants, i.e., surfactants which are particularly tolerated by skin, are fatty alcohol polyglycol ether-sulphates, monoglyceride sulphates, mono- and/or dialkyl sulphosuccinates, fatty acid isethionates, fatty acid sarcosinates, fatty acid taurides, fatty acid glutamates, ether-carboxylic acids, alkyl oligoglucosides, fatty acid glucamides, alkylamidobetaines and/or protein-fatty acid condensates, the latter for example based on wheat proteins.

It is furthermore possible to employ amphoteric surfactants, such as, e.g., betaines, amphoacetates or amphopropionates, thus, e.g., substances such as the N-alkyl-N,N-dimethylammonium glycinates, for example coco-alkyldimethylammonium glycinate, N-acylaminopropyl-N,N-dimethylammonium glycinates, for example coco-acylamimopropyl-dimethylammonium glycinate, and 2-alkyl-3-carboxymethyl-3-hydroxyethylimidazolines having in each case 8 to 18 C atoms in the alkyl or acyl group, and coco-acylaminoethylhydroxyethylcarboxymethyl glycinate.

Of the ampholytic surfactants, those surface-active compounds which contain, apart from a $C_{8/18}$-alkyl or -acyl group, at least one free amino group and at least one —COOH or —SO$_3$H group in the molecule and are capable of formation of inner salts can be employed. Examples of suitable ampholytic surfactants are N-alkylglycines, N-alkylpropionic acids, N-alkylaminobutyric acids, N-alkyliminodipropionic acids, N-hydroxyethyl-N-alkylamido-propylglycines, N-alkyltaurines, N-alkylsarcosines, 2-alkylaminopropionic acids and alkylaminoacetic acids having in each case about 8 to 18 C atoms in the alkyl group. Further examples of ampholytic surfactants are N-coco-alkylaminopropionate, coco-acylaminoethyl-aminopropionate and $C_{12/18}$-acrylsarcosine.

Suitable thickeners are, for example, polysaccharides, in particular xanthan gum, guar-guar, agar-agar, alginates and tyloses, carboxymethylcellulose and hydroxyethylcellulose, furthermore higher molecular weight polyethylene glycol mono- and diesters of fatty acids, polyacrylates (e.g., Carbopols™ or Synthalens™), polyacrylamides, polyvinyl alcohol and polyvinylpyrrolidone, surfactants, such as, for example, ethoxylated fatty acid glycerides, esters of fatty acids with polyols, such as, for example, pentaerythritol or trimethylolpropane, fatty alcohol ethoxylates with a restricted distribution of homologues or alkyl oligoglucosides, and electrolytes, such as sodium chloride and ammonium chloride.

Possible thickeners for thickening oily phases are all the thickening agents known to one skilled in the art. In this context, there may be mentioned waxes, such as hydrogenated castor wax, beeswax or microwax. Inorganic thickening agents can also be employed, such as silica, alumina or laminar silicates (e.g., hectorite, laponite, saponite). In this context, these inorganic thickeners for the oily phase can be hydrophobically modified. In this context, Aerosils, laminar silicates and/or metal salts of fatty acids, such as, e.g., zinc stearate, can be employed for thickening/stabilizing water-in-oil emulsions.

The formulations can comprise as viscosity regulators for aqueous surfactant systems, e.g., NaCl, low molecular weight nonionic surfactants, such as Cocoamide DEA/MEA and Laureth-3, or polymeric, high molecular weight, associative, highly ethoxylated fat derivatives, such as PEG-200 Hydrogenated Glyceryl Palmate.

UV light protection filters, which can be employed are, for example, organic substances that are capable of absorbing ultraviolet rays and of releasing the energy absorbed again in the form of longer-wavelength radiation, e.g., heat. UVB filters can be oil-soluble or water-soluble. Oil-soluble UVB light protection filters which may be mentioned include, but are not limited to:

3-benzylidenecamphor and derivatives thereof, e.g., 3-(4-methylbenzylidene)camphor (INCI: 4-Methylbenzylidene Camphor, trade name: Eusolex 6300), 4-aminobenzoic acid derivatives, such as, e.g., 4-(dimethylamino)-benzoic acid 2-ethylhexyl ester, 4-(dimethylamino) benzoic acid 2-ethylhexyl ester and 4-(dimethylamino)benzoic acid amyl ester, ester of cinnamic acid, such as, e.g., 4-methoxycinnamic acid 2-ethylhexyl ester (INCI: Octyl Methoxycinnamate, trade name: Parsol® MCX), 4-methoxycinnamic acid isopentyl ester, 2-ethylhexyl 2-cyano-3,3-diphenylacrylate (INCI: Octocrylene; trade name: Uvinul N-539), esters of salicylic acid, such as, e.g., salicylic acid 2-ethylhexyl ester, salicylic acid 4-isopropylbenzyl ester, salicylic acid homomethyl ester, derivatives of benzophenone, such as, e.g., 2-hydroxy-4-methoxybenzophenone, 2-hydroxy-4-methoxy-4'-methylbenzophenone, 2,2'-dihydroxy-4-methoxybenzophenone, 2-(4'-diethylamino-2'-hydroxybenzoyl)-benzoic acid hexyl ester (also: aminobenzophenone), esters of benzalmalonic acid, such as, e.g., 4-methoxybenzmalonic acid di-2-ethylhexyl ester, triazine derivatives, such as, e.g., 4,4',4''-(1,3,5-triazine-2,4,6-triyltriimino)-tris-benzoic acid tris(2-ethylhexyl ester) (also: 2,4,6-tris-[anilino-(p-carbo-2'-ethyl-1'-hexyloxy)]-1,3,5-triazine, INCI: Octyl Triazone, marketed by BASF Aktiengesellschaft under the trade name UVINUL® T 150), 2,4-bis-{[4-(2-ethyl-hexyloxy)-2-hydroxy]-phenyl}-6-(4-methoxyphenyl)-1,3,5-triazine (INCI: Aniso Triazine, obtainable under the trade name Tinosorb® S), dioctylbutylamidotriazone (INCI: Dioctylbutamidotriazone), 2,4-bis-[5-1 (dimethylpropyl)benzoxazol-2-yl-(4-phenyl)-imino]-6-(2-ethylhexyl)-imino-1,3,5-triazine with the CAS no. 288254-16-0, obtainable from 3V Sigma under the trade name Uvasorb® K2A), 2,4-bis-{[4-(2-ethyl-hexyloxy)-2-hydroxy]-phenyl}-6-(4-methoxyphenyl)-1,3,5-triazine (INCI: Bis-ethylhexyloxylphenol Methoxyphenyl Triazine), obtainable under the trade name Tinosorb® S from CIBA-Chemikalien GmbH and 2-[4,6-bis(2,4-dimethylphenyl)-1,3,5-triazin-2-yl]-5-(octyloxy)phenol (CAS no.: 2725-22-6), propane-1,3-diones, such as, e.g., 1-(4-tert-butylphenyl)-3-(4'-methoxyphenyl)propane-1,3-dione.

A further UV-B filter is 3-(4-(2,2-bis(ethoxycarbonylvinyl)-phenoxy)propenyl)-methoxysiloxane/dimethylsiloxane copolymer, which is obtainable, for example, under the trade name Parsol® SLX.

Possible water-soluble UVB light protection filters are, for example:

salts of 2-phenylbenzimidazole-5-sulphonic acid, such as its alkali metal, alkaline earth metal, ammonium, alkylammonium, alkanolammonium and glucammonium salts, and the sulphonic acid itself with the INCI name Phenylbenzimidazole Sulphonic Acid (trade name: Eusolex 232), 1,4-di(2-oxo-10-sulpho-3-bornylidenemethyl)-benzene (also: 3,3'-(1,4-Phenylenedimethylene)-bis-(7,7-dimethyl-2-oxo-bicyclo-[2.2.1]hept-1-ylmethane Sulphonic Acid) and salts thereof (especially the corresponding 10-sulphato compounds, in particular the corresponding sodium, potassium or triethanolammonium salt), which is also called benzene-1,4-di(2-oxo-3-bornylidenemethyl-10-sulphonic acid) and has the INCI name Terephthalidene Dicamphor Sulphonic Acid (CAS no.: 90457-82-2), phenylene-1,4-bis-(2-benzimidazyl)-3,3'-5,5'-tetrasulphonic acid and its salts, the corresponding sodium, potassium or triethanolammonium salts, e.g., phenylene-1,4-bis-(2-benzimidazyl)-3,3'-5,5'-tetrasulphonic acid bis-sodium salt with the INCI name Bisimidazylate, trade name: Neoheliopan® AP (CAS no.: 180898-37-7), sulphonic acid derivatives of benzophenone, such as, e.g., 2-hydroxy-4-methoxybenzophenone-5-sulphonic acid and its salts, sulphonic acid derivatives of 3-benzylidenecamphor, such as, e.g., 4-(2-oxo-3-bornylidenemethyl)benzenesulphonic acid and 2-methyl-5-(2-oxo-3-bornylidene)sulphonic acid and salts thereof.

Possible typical UVA light protection filters are, for example, derivatives of benzoylmethane, such as, for example, 1-(4'-tert-butylphenyl)-3-(4'-methoxyphenyl)propane-1,3-dione (4-(tert-butyl)-4'-methoxydibenzoylmethane, INCI:

Butylmethoxydibenzoylmethane, trade name: Parsol 1789) or 1-phenyl-3-(4'-isopropylphenyl)propane-1,3-dione.

The UV-A and UV-B filters can of course also be employed in mixtures.

Further UV filter substances that can be employed are so-called broad-band filters, i.e., filter substances which absorb both UV-A and UV-B radiation.

Examples of these are, inter alia:

2,2'-methylene-bis-(6-(2H-benzotriazol-2-yl)-4-(1,1,3,3-tetramethylbutyl)-phenol) (Tinosorb® M, CIBA-Chemikalien GmbH), benzene-1,4-di(2-oxo-3-bornylidenemethyl-10-sulphonic acid) (INCI: Terephthalidene Dicamphor Sulphonic Acid, trade name: Mexoryl® SX), 2-(2H-benzotriazol-2-yl)-4-methyl-6-[2-methyl-3-[1,3,3,3-tetramethyl-1-[(trimethyl-silyl)oxy]disiloxanyl]propyl]-phenol (INCI: Drometrizole Trisiloxane, trade name: Mexoryl® XL).

In addition to the soluble substances mentioned, insoluble pigments, namely finely disperse metal oxides and salts, are also possible for this purpose, such as, for example, titanium dioxide, zinc oxide, iron oxide, aluminium oxide, cerium oxide, zirconium oxide, silicates (talc), barium sulphate and zinc stearate. In this context, the particles should have an average diameter of less than 100 nm, e.g., between 5 and 50 nm and in particular between 15 and 30 nm. The particles can have a spherical shape, but those particles which have an ellipsoid shape or a shape which deviates otherwise from the spherical can also be employed. Micronized organic pigments, such as, for example, 2,2'-methylene-bis-{6-(2H-benzotriazole-2-yl)-4-(1,1,3,3-tetramethylbutyl)-phenol} having a particle size of <200 nm, which is obtainable, e.g., as a 50% strength aqueous dispersion, are a relatively novel class of light protection filters.

Further suitable UV light protection filters can also be found in the overview by P. Finkel in SÖFW-Journal 122, 543 (1996).

In addition to the two abovementioned groups of primary UV light protection filters, secondary light protection agents of the antioxidant type which interrupt the photochemical reaction chain triggered when UV radiation penetrates into the skin can also be employed. Antioxidants that can be employed are, e.g., superoxide dismutase, tocopherols (vitamin E), dibutylhydroxytoluene and ascorbic acid (vitamin C).

Hydrotropic agents, which can be employed for improving the flow properties and the use properties, are, for example, ethanol, isopropyl alcohol or polyols. Polyols, which are possible here, can have 2 to 15 carbon atoms and at least two hydroxyl groups. Typical examples are:

glycerol, alkylene glycols, such as, for example, ethylene glycol, diethylene glycol, propylene glycol, butylene glycol, hexylene glycol and polyethylene glycols having an average molecular weight of from 100 to 1,000 Dalton, technical-grade oligoglycerol mixtures having a degree of self-condensation of from 1.5 to 10, such as, for example, technical-grade diglycerol mixtures having a diglycerol content of from 40 to 50 wt. %, methylol compounds, such as, in particular, trimethylolethane, trimethylolpropane, trimethylolbutane, pentaerythitol and dipentaerythritol, lower alkyl glucosides, in particular those having 1 to 4 carbon atoms in the alkyl radical, such as, for example, methyl and butyl glucoside, sugar alcohols having 5 to 12 carbon atoms, such as, for example, sorbitol or mannitol, sugars having 5 to 12 carbon atoms, such as, for example, glucose or sucrose, amino sugars, such as, for example, glucamine.

Solids that can be employed are, for example, iron oxide pigments, titanium dioxide or zinc oxide particles and those additionally mentioned under "UV stabilizers". Particles that lead to specific sensorial effects can also be employed, such as, for example, nylon 12, boron nitride, polymer particles, such as, for example, polyacrylate or polymethacrylate particles, or silicone elastomers. Fillers which can be employed include starch and starch derivatives, such as tapioca starch, distarch phosphate, aluminium- or sodium-starch, octenyl succinate and pigments which have neither a chiefly UV filter, nor a coloring action, for example Aerosile® (CAS no. 7631-86-9).

Film-forming agents for improving the water resistance, which can be employed are, for example: polyurethanes, Dimethicone Copolyol, polyacrylates or PVP/VA copolymer (PVP=polyvinylpyrrolidone, VA=vinyl acetate). Fat-soluble film-forming agents which can be employed are: e.g., polymers based on polyvinylpyrrolidone (PVP), copolymers of polyvinylpyrrolidone, PVP/hexadecene copolymer or PVP/eicosene copolymer.

Pearlescent additives which can be employed are, e.g., glycol distearates or PEG-3 Distearate.

Possible deodorant active compounds are, e.g., odor maskers, such as the usual perfume constituents, odor absorbers, for example the laminar silicates described in the patent laid-open specification DE 40 09 347, and of these in particular montmorillonite, kaolinite, ilite, beidelite, nontronite, saponite, ilectorite, bentonite, smectite, furthermore, for example, zinc salts of ricinoleic acid. Germ-inhibiting substances are likewise suitable for incorporation. Germ-inhibiting substances are, for example, 2,4,4'-trichloro-2'-hydroxydiphenyl ether (Irgasan), 1,6-di-(4-chlorophenylbiguanido)-hexane (chlorhexidine), 3,4,4'-trichlorocarbanilide, quaternary ammonium compounds, clove oil, mint oil, thyme oil triethyl citrate, farnesol, (3,7,11-trimethyl-2,6,10-dodecatrien-1-ol), ethylhexyl glyceryl ether, polyglyceryl-3 caprylate (TEGO® Cosmo P8137 Evonik Degussa), and the active agents described in the patent laid-open specifications DE 198 55 934, DE 37 40 186, DE 39 38 140, DE 42 04 321, DE 42 29 707, DE 42 29 737, DE 42 38 081, DE 43 09 372, DE 43 24 219 and EP 0 666 732.

Antiperspirant active compounds which can be employed are astringents, for example basic aluminium chlorides, such as aluminium chlorohydrate ("ACH") and aluminium zirconium glycine salts ("ZAG").

Insect repellents which can be employed are, for example, N,N-diethyl-m-toluamide, 1,2-pentanediol, or Insect Repellent 3535.

Self-tanning agents which can be employed are, e.g., dihydroxyacetone and erythrulose.

Preservatives that can be employed are, for example, mixtures of individual or several alkylparaben esters with phenoxyethanol. The alkylparaben esters can be methylparaben, ethylparaben, propylparaben and/or butylparaben. Instead of phenoxyethanol, other alcohols, such as, for example, benzyl alcohol or ethanol, can also be employed. Other conventional preservatives can also be employed, such as, for example, sorbic or benzoic acid, salicylic acid, 2-bromo-2-nitropropane-1,3-diol, chloroacetamide, Diazolidinyl Urea, DMDM Hydantoin, Iodopropynyl Butyl Carbamate, Sodium Hydroxymethylglycinate, methyl-isothiazoline, chloromethyl-isothiazoline, ethylhexylglycerol or Caprylyl Glycol.

Conditioning agents which can be used are, e.g., organic quaternary compounds, such as cetrimonium chloride, dicetyldimonium chloride, behenyltrimonium chloride, distearyldimonium chloride, behenyltrimonium methosulphate, distearoylethyldimonium chloride, palmitamidopropyltrimonium chloride, Guar Hydroxypropyltrimonium Chloride, Hydroxypropyl-guar, Hydroxypropyltrimonium Chloride or Quaternium-80, or also amine derivatives, such as, e.g., aminopropyldimethicone or stearamidopropyldimethylamine.

Perfumes that can be employed are natural or synthetic odoriferous substance or mixtures thereof. Natural odoriferous substances are extracts from blossom (lily, lavender, rose, jasmine, orange-blossom, ylang-ylang), stems and leaves (geranium, patchouli, petitgrain), fruit (aniseed, coriander, caraway, juniper), fruit peel (bergamot, lemon, orange), roots (mace, angelica, celery, cardamom, costus, iris, thyme), needles and branches (spruce, fir, pine, dwarf pine), resins and balsams (galbanum, elemi, benzoin, myrrh, frankincense, opoponax). Animal raw materials are possible, such as, for example, civet and castoreum. Typical synthetic odoriferous compounds are products of the ester, ether, aldehyde, ketone, alcohol and hydrocarbon type. Odoriferous compounds of the ester types are, e.g., benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethyl-phenylglycinate, allyl cyclohexylpropionate, styrallyl propionate and benzyl salicylate. The ethers include, for example, benzyl ethyl ether, the aldehydes include, e.g., the linear alkanals having 8 to 18 carbon atoms, citral, citronellal, citronellyloxyacetaldehyde, cyclamen aldehyde, hydroxycitronellal, lilial and bourgeonal, the ketones include, e.g., the ionones, α-isomethylionone and methyl cedryl ketone, the alcohols include anethole, citronellol, eugenol, isoeugenol, geraniol, linalool, phenylethyl alcohol and terpineol, the hydrocarbons include chiefly the terpenes and balsams. Mixtures of various odoriferous substances which together generate a pleasant fragrance can be employed. Essential oils of low volatility, which are usually employed as aroma components, are also suitable as perfumes, e.g., sage oil, chamomile oil, clove oil, Melissa oil, mint oil, cinnamon leaf oil, linden blossom oil, juniper berry oil, vetiver oil, frankincense oil, galbanum oil, labolanum oil and lavandin oil. Bergamot oil, dihydromyrcenol, lilial, lyral, citronellol, phenylethyl alcohol, α-hexylcinnamaldehyde, geraniol, benzylacetone, cyclamen aldehyde, linalool, Boisambrene Forte, ambroxan, indole, hedione, sandelice, lemon oil, mandarin oil, orange oil, allyl amylglycollate, cyclovertal, lavandin oil, clary sage oil, β-damascone, Bourbon geranium oil, cyclohexyl salicylate, Vertofix Coeur, Iso-E-Super, Fixolide NP, evernyl, iraldein gamma, phenylacetic acid, geranyl acetate, benzyl acetate, rose oxide, romilate, irotyl and floramate, by themselves or in mixtures, can be employed.

Dyestuffs which can be employed are the substances that are suitable and approved for cosmetic purposes, such as are summarized, for example, in the publication "Kosmetische Färbemittel [Cosmetic Coloring Agents]" of the Dyestuffs Commission of the Deutsche Forschungsgemeinschaft, Verlag Chemie, Weinheim, 1984, p. 81 to 106. These dyestuffs are conventionally employed in concentrations of from 0.001 to 0.1 wt. %, based on the total mixture.

Biogenic active compounds are to be understood as meaning, for example, tocopherol, tocopherol acetate, tocopherol palmitate, ascorbic acid, deoxyribonucleic acid, coenzyme Q10, retinol, bisabolol, allantoin, phytantriol, panthenol, AHA acids, amino acids, hyaluronic acid, alpha-hydroxy acids, polyglutamic acid, creatine (and creatine derivatives), guanidine (and guanidine derivatives), ceramides, phytosphingosine (and phytosphingosine derivatives), sphingosine (and sphingosine derivatives), pseudoceramides, essential oils, peptides, protein hydrolysates, plant extracts, sphingolipids and vitamin complexes.

Care additives which the formulations can comprise include, e.g., ethoxylated glycerol fatty acid esters, such as, for example, PEG-7 Glycerin Cocoate, or cationic polymers, such as, for example, Polyquaternium-7 or polyglycerol esters.

Super-oiling agents which can be used are substances such as, for example, lanolin and lecithin and polyethoxylated or acylated lanolin and lecithin derivatives, polyol fatty acid esters, monoglycerides and fatty acid alkanolamides, the latter simultaneously serving as foam stabilizers.

Solvents which can be employed are, e.g., aliphatic alcohols, such as ethanol, propanol or 1,3-propanediol, cyclic carbonates, such as ethylene carbonate, propylene carbonate, glycerol carbonate, esters of mono- or polycarboxylic acids, such as ethyl acetate, ethyl lactate, dim ethyl adipate and diethyl adipate, propylene glycol, dipropylene glycol, glycerol, glycerol carbonate or water.

The use according to the invention is suitable in particular for the preparation of sunscreen preparations.

The invention therefore also provides the use of isononyl benzoate, preferably of one or more substances of the formula (I), with the proviso that the nonyl alcohols obtained by hydrolysis of the substance(s) used contain less than 80 mol %, preferably less than 40 mol % and particularly preferably less than 10 mol % of 3,5,5-trimethylhexanol, in cosmetic, dermatological or pharmaceutical formulations as solubilizing agents or solvents for at least one UV light protection filter substance.

An additional component, which is preferably employed, is therefore also the group of UV light protection filter substances. The lipophilic, hydrophobic UV light protection filter substance, in particular triazine derivatives, are preferably employed here.

UV-B filters which are particularly preferably employed here are the UV light protection filter substances 2-cyano-3-phenyl-cinnamic acid 2-ethylhexyl ester, 2,4-bis-{[4-(2-ethyl-hexyloxy)-2-hydroxy]-phenyl}-6-(4-methoxyphenyl)-1,3,5-triazine, dioctylbutylamidotriazone, 2-hydroxy-4-methoxybenzophenone, 2-hydroxy-4-methoxy-4'-methylbenzophenone, 2,2'-dihydroxy-4-methoxybenzophenone, 4-methoxybenzmalonic acid di-2-ethylhexyl ester, 2,4,6-tris-[anilino-(p-carbo-2'-ethyl-1'-hexyloxy)]-1,3,5-triazine, 2,4-bis-[5-(dimethylpropyl)benzoxazol-2-yl-(4-phenyl)-imino]-6-(2-ethylhexyl)-imino-1,3,5-triazine, 2,4-Bis-{[4-(2-ethyl-hexyloxy)-2-hydroxy]-phenyl}-6-(4-methoxyphenyl)-1,3,5-triazine and 2-[4,6-Bis(2,4-dimethylphenyl)-1,3,5-triazin-2-yl]-5-(octyloxy) phenol.

UV-A filters which are preferably employed are 1-(4'-tert-butylphenyl)-3-(4'-methoxyphenyl)-propane-1,3-dione, 1-phenyl-3-(4'-isopropylphenyl)propane-1,3-dione.

Particularly preferred UV-A filters are 4-(tert-butyl)-4'-methoxydibenzoylmethane (CAS no. 70356-09-1), which is sold by Givaudan under the trademark Parsol® 1789 and by Merck under the trade name Eusolex® 9020, and hydroxybenzophenones according to DE 102004027475, particularly preferably 2-(4'-diethylamino-2'-hydroxybenzoyl)-benzoic acid hexyl ester (also: aminobenzophenone), which is obtainable under the name Uvinul A Plus from BASF.

UV filter substances which are highly preferred are the so-called broad-band filters, i.e., filter substances which absorb both UV-A and UV-B radiation. Within this group, 2,2'-methylene-bis-(6-(2H-benzotriazol-2-yl)-4-(1,1,3,3-tetramethylbutyl)-phenol, which is obtainable under the trade name Tinosorb® M from CIBA-Chemikalien GmbH, and 2-(2H-benzotriazol-2-yl)-4-methyl-6-[2-methyl-3-[1,3,3,3-tetramethyl-1-[(trimethylsilyl)oxy]-disiloxanyl]propyl]-phenol (CAS no.: 155633-54-8) with the INCI name Drometrizole Trisiloxane, are preferably employed.

The amount of UV light protection filters employed is preferably 0.01-15%? preferably 0.05-10%, particularly preferably 0.1-5%, based on the formulation.

The use of a combination of several different UV filters is preferred.

A further additional component which is preferably employed is the group of film-forming agents, in order to improve the water resistance of the compositions and therefore also to increase the UV protection performance. Film-forming agents which are preferably employed are polyurethanes, Dimethicone Copolyol, polyacrylates, PVP/VA copolymer (PVP polyvinylpyrrolidone, VA=vinyl acetate), polyvinylpyrrolidone (PVP), copolymers of polyvinylpyrrolidone, PVP/hexadecene copolymer or PVP/eicosene copolymer.

A further additional component which is preferably employed is the group of deodorant and antiperspirant active compounds. From this group, astringents are preferably employed, particularly preferably basic aluminium chlorides, such as aluminium chlorohydrate ("ACH") or aluminium zirconium glycine salts ("ZAG").

The invention moreover provides cosmetic, dermatological or pharmaceutical formulations comprising a substance of the general formula (I), wherein $R_1$ is an unbranched or branched $C_9$-alkyl radical.

Formulations according to the invention can be used, for example, as a skin care, face care, head care, body care, intimate care, foot care, hair care, nail care, dental care or oral care product.

Formulations according to the invention can be used, for example, in the form of an emulsion, a suspension, a solution, a cream, an ointment, a paste, a gel, an oil, a powder, an aerosol, a stick, a spray, a cleansing product, a make-up or sunscreen preparation or a face lotion.

Preferably, the cosmetic, dermatological or pharmaceutical formulations comprise 0.1 to 60 percent by weight, preferably 1 to 25 percent by weight and particularly preferably 3 to 15 percent by weight of at least one substance of the general formula (I).

The cosmetic, dermatological or pharmaceutical formulations particularly preferably comprise one or more substances of the formula (I), with the proviso that the nonyl alcohols obtained by hydrolysis of the substance(s) used contain less than 80 mol %, preferably less than 40 mol % and particularly preferably less than 10 mol % of 3,5,5-trimethylhexanol.

Particularly preferred cosmetic, dermatological or pharmaceutical formulations comprise:
  (a) 0.1-60 percent by weight of at least one substance of the formula (I), preferably of one or more substances of the formula (I), with the proviso that the nonyl alcohols obtained by hydrolysis of the substance(s) used contain less than 10 mol % of 3,5,5-trimethylhexanol.
  (b) 0.1-20 percent by weight of surfactants and/or emulsifiers and/or coemulsifiers,
  (c) 0.1-40 percent by weight of further oil substances, and
  (d) 0-98 percent by weight of water,
wherein the percentages by weight of components (a), (b), (c) and (d) add up to 100 percent by weight.

In the examples given below, the present invention is described by way of example without the intention being for the invention, the scope of use of which emerges from the entire description and the claims, to be limited to the embodiments mentioned in the examples.

EXAMPLES

Example 1

Dissolving Power

Four representative UV-A or UV-B light protection filters were chosen as representatives for testing the dissolving power for crystalline UV light protection filters in isononyl benzoate (Vestinol® INB, Evonik Oxeno GmbH). These were Benzophenone-3 (2-hydroxy-4-methoxy-benzophenone, BP-3), Butyl Methoxydibenzoylmethane (BMDM), Octyl Triazone (2,4,6-trianilino-p-(carbo-2'-ethylhexyl-1'-oxy)-1,3,5-triazine, EHT) and bemotrizinol (Bis-ethylhexyloxyphenol Methoxyphenyl Triazine, BEMT).

The dissolving power of conventional ester oils for these compounds was not satisfactory in most cases. A compound with a good dissolving power for UV light protection filter substances was Tegosoft® TN, which is also widely established as an ingredient for sunscreen formulations.

For determination of the dissolving power for these three UV light protection filters, in each case a particular amount (50 g) of one of the compounds according to the invention was initially introduced into the dissolving vessel and temperature-controlled at 22° C. 1 percent by weight of a UV light protection filter was then added and the mixture was stirred until this amount had dissolved completely and homogeneously. This operation was repeated until the maximum amount of the UV light protection filter which can be dissolved had been exceeded. For complete dissolving, a relatively long stirring time of several hours was often necessary at higher concentrations.

Once the maximum concentration had been roughly determined in this manner, the test was repeated with smaller weights of the UV light protection filter for fine determination of the concentration range around this maximum concentration.

The compound Tegosoft® TN (C12-15 Alkyl Benzoate) was used as a reference.

| Product | (UV filter) | | | |
| --- | --- | --- | --- | --- |
| | BP-3 | BMDM | EHT | BEMT |
| Tegosoft ® TN (C12-15 Alkyl Benzoate) | 15% | 13% | 4% | 9% |
| Isononyl Benzoate | 21% | 14% | 6% | 12% |

As can be seen from the above values, the dissolving power of the compounds according to the invention was significantly better than the dissolving power of Tegosoft® TN in many cases.

Example 2

Cosmetic Formulations

The cosmetic emulsions described were intended to serve to illustrate the usability of isononyl benzoate in cosmetic emulsions by way of example.

In this context, isononyl benzoate can be employed both in oil-in-water and in water-in-oil emulsions. Cosmetic emulsions both of liquid and of paste-like consistency can furthermore be prepared with isononyl benzoate both in hot processes and in cold processes. The preparation and homogenization steps were carried out by conventional methods, Vestinol® INB, Evonik Oxeno GmbH was always employed as the isononyl benzoate.

Formulation Example 1

O/W Care Cream (Hot Preparation)

|  | % w/w |
|---|---|
| AXOL ® C 62 | 1.5 |
| TEGIN ® M | 2.0 |
| TEGO ® Alkanol 1618 | 3.0 |
| Isononyl Benzoate | 4.7 |
| TEGOSOFT ® CR | 2.0 |
| TEGOSOFT ® TIS | 1.0 |
| TEGOSOFT ® MM | 0.5 |
| Cyclomethicone | 4.0 |
| *Macadamia Ternifolia* Seed Oil | 2.0 |
| Tocopheryl Acetate | 0.5 |
| Glycerin | 4.0 |
| Panthenol | 0.5 |
| Allantoin | 0.2 |
| Water | 65.5 |
| TEGO ® Carbomer 134 | 0.3 |
| Bisabolol | 0.5 |
| NaOH (10% strength aqueous solution) | 0.8 |
| Ethanol | 7.0 |
| Perfume, preservative | q.s. |

Formulation Example 2

O/W Body Lotion (Cold Preparation)

|  | % w/w |
|---|---|
| TEGO ® Care LTP | 2.0 |
| Isononyl Benzoate | 7.3 |
| TEGOSOFT ® CT | 6.5 |
| TEGO ® Carbomer 141 | 0.1 |
| TEGO ® 341 ER | 0.1 |
| Glycerin | 3.0 |
| Water | 80.4 |
| NaOH (10% strength aqueous solution) | 0.6 |
| Perfume, preservative | q.s. |

Formulation Example 3

O/W Day Cream (Hot Preparation)

|  | % w/w |
|---|---|
| TEGO ® Care 450 | 3.0 |
| TEGIN ® M | 2.0 |
| TEGO ® Alkanol 18 | 1.0 |
| Isononyl Benzoate | 4.5 |
| TEGOSOFT ® Liquid | 9.5 |
| TEGOSOFT ® P | 7.5 |
| Ethylhexyl Methoxycinnamate | 2.0 |
| Tocopheryl Acetate | 0.5 |
| Glycerin | 3.0 |
| Water | 66.2 |
| TEGO ® Carbomer 134 | 0.2 |
| NaOH (10% strength aqueous solution) | 0.6 |
| Perfume, preservative | q.s. |

Formulation Example 4

W/O Body Lotion

|  | % w/w |
|---|---|
| ISOLAN ® GPS | 3.0% |
| Hydrogenated Castor Wax | 0.25% |
| Microcrystalline Wax | 0.25% |
| Isononyl Benzoate | 10.7% |
| TEGOSOFT ® DEC | 10.0% |
| Tocopheryl Acetate | 0.6% |
| TEGO ® Cosmo C 100 | 0.5% |
| Panthenol | 0.5% |
| Glycerin | 3.0% |
| Water | 70.2% |
| $MgSO_4 * 7 H_2O$ | 1.0% |
| Perfume, preservative | q.s. |

Formulation Example 5

W/O Sunscreen Formulations

|  | No. 5.1 % w/w | No. 5.2 % w/w | No. 5.3 % w/w |
|---|---|---|---|
| ISOLAN ® GPS | 3.0 | 3.0 | 3.0 |
| Hydrogenated Castor Wax | 0.2 | 0.2 | 0.2 |
| Microcrystalline Wax | 0.2 | 0.2 | 0.2 |
| Isononyl Benzoate | 13.5 | 13.5 | 7.6 |
| Octocrylene | — | — | 8.0 |
| Ethylhexyl Methoxycinnamate | 4.0 | — | — |
| Ethylhexyl Salicylate | — | — | 5.0 |
| Butyl Methoxydibenzoylmethane | 3.0 | — | 2.0 |
| TEGO ® Sun TDEC 45 | 11.0 | 11.0 | — |
| TEGO ® Sun Z 500 | — | 3.0 | — |
| Isostearic Acid | — | 1.0 | — |
| Water | 61.5 | 64.6 | 70.5 |
| Glycerin | 2.0 | 2.0 | 2.0 |
| MgSO4*7H2O | 1.5 | 1.5 | 1.5 |
| Perfume, preservative | q.s. | q.s. | q.s. |
| SPF (optometrics) | 38 | 11 | 20 |

Formulation Example 6

O/W Sunscreen Lotion

|  | No. 6.1 % w/w | No. 6.2 % w/w | No. 6.3 % w/w | No. 6.4 % w/w |
|---|---|---|---|---|
| Axol ® C 62 | 2.0 | 2.5 | — | — |
| TEGO ® Alkanol 1618 | 1.0 | 1.0 | — | 1.0 |
| TEGO Care 450 | — | — | 3.0 | 3.0 |
| TEGIN ® M | — | — | — | 2.0 |
| Isononyl Benzoate | 9.0 | 5.5 | 8.5 | 16.5 |
| Jojoba Oil | — | — | 2.5 | 2.0 |

-continued

| | No. 6.1 % w/w | No. 6.2 % w/w | No. 6.3 % w/w | No. 6.4 % w/w |
|---|---|---|---|---|
| Tocopheryl Acetate | 0.5 | 0.5 | — | — |
| TEGO ® Sun TDEC 45 | 5.0 | — | — | — |
| TEGO ® Sun T 805 | — | 3.0 | — | — |
| TEGO ® Sun Z 500 | — | — | — | 5.0 |
| Ethylhexyl Methoxycinnamate | 7.0 | 7.0 | 7.5 | — |
| Ethylhexyl Salicylate | — | — | 5.0 | — |
| Butyl Methoxydibenzoylmethane | 3.0 | 2.0 | — | — |
| Benzophenone-3 | — | — | 5.0 | — |
| Menthyl Anthranilate | — | — | 5.0 | — |
| Bis-ethylhexyloxyphenol Methoxyphenyl Triazine | — | — | — | 3.0 |
| Xanthan Gum | — | 0.3 | — | — |
| Glycerin | 2.0 | 2.0 | — | — |
| Sodium Hexametaphosphate (Graham's Salt) | — | — | — | 0.2 |
| Water | 68.9 | 74.6 | 61.45 | 63.9 |
| Tego ® Carbomer 141 | 0.2 | 0.2 | 0.25 | — |
| TEGOSOFT ® TN | 0.8 | 0.8 | 1.0 | — |
| NaOH (10% strength aqueous solution) | 0.6 | 0.6 | 0.8 | — |
| $ZnSO_4 * 7 H_2O$ | — | — | — | 0.4 |
| Perfume, preservative | q.s. | q.s. | q.s. | q.s. |
| SPF (optometrics) | 48 | 35 | 30 | 15 |

Formulation Example 7

O/W Sunscreen Cream (Cold Preparation)

| | % w/w |
|---|---|
| ABIL ® Care 85 | 2.0 |
| Isononyl Benzoate | 5.5 |
| TEGOSOFT ® DC | 3.0 |
| Tocopheryl Acetate | 0.5 |
| Isoamyl Methoxycinnamate | 4.0 |
| Ethylhexyl Methoxycinnamate | 4.0 |
| Octocrylene | 4.0 |
| Butyl Methoxydibenzoylmethane | 2.0 |
| TEGO ® SMO 80V | 1.0 |
| Glycerin | 2.0 |
| Water | 71.1 |
| TEGO ® Carbomer 141 | 0.05 |
| TEGO ® Carbomer 341ER | 0.05 |
| TEGOSOFT ® DC | 0.4 |
| NaOH (10% strength aqueous solution) | 0.4 |
| Perfume, preservative | q.s. |
| SPF (optometrics) | 35 |

Formulation Example 8

O/W Sunscreen Spray

| | % w/w |
|---|---|
| Isononyl Benzoate | 5.6 |
| TEGOSOFT ® DC | 2.5 |
| Tocopheryl Acetate | 0.5 |
| Ethylhexyl Methoxycinnamate | 5.0 |
| Octocrylene | 3.0 |
| Butyl Methoxydibenzoylmethane | 2.0 |
| TEGO ® Care CG 90 | 1.0 |
| Glycerin | 2.0 |
| Water | 77.5 |
| TEGO ® Carbomer 141 | 0.05 |
| TEGO ® Carbomer 341ER | 0.05 |
| TEGOSOFT ® DC | 0.4 |

-continued

| | % w/w |
|---|---|
| NaOH (10% strength aqueous solution) | 0.4 |
| Perfume, preservative | q.s. |
| SPF (optometrics) | 13 |

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claim is:

1. A method for the preparation of an oil in water formulation comprising:

adding at least one substance of the general formula (I)

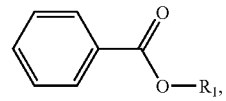

(I)

wherein general formula (I) is isononyl benzoate, to at least one component selected from the group consisting of an emollient, emulsifier, surfactant, thickener, viscosity regulator, stabilizer, UV light protection filter, antioxidant, hydrotropic agent, filler, film-forming agent, pearlescent additive, deodorant active compound, antiperspirant active compound, insect repellent, self-tanning agent, preservative, conditioning agent, perfume, dyestuff, biogenic active compound, care additive, superoiling agent, and solvent, with the proviso that nonyl alcohols obtained by hydrolysis of the at least one substance of general formula (I) contain less than 80 mol % of 3,5,5-trimethylhexanol, wherein the formulation comprises (a) 0.1-60 percent by weight of the at least one substance of the general formula (I),
(b) 0.1-20 percent by weight of surfactants and/or emulsifiers and/or coemulsifiers,
(c) 0.1-40 percent by weight of further oil substances,
(d) 0-98 percent by weight of water,
wherein the percentages by weight of components (a), (b), (c) and (d) add up to 100 percent by weight to form the oil in water formulation.

2. The method of claim 1 wherein that at least one component is at least one UV light protection filter substance, and said at least one substance of formula (I) serves as a solubilizing agent or solvent for said at least one UV light protection filter substance.

3. The method of claim 2 wherein the at least one of the UV light protection filter substance is a triazine derivative.

4. The method of claim 2 wherein the at least one of the UV light protection filter substances is selected from the group of compounds consisting of
2-cyano-3-phenyl-cinnamic acid 2-ethylhexyl ester,
2,4-bis-{[4-(2-ethyl-hexyloxy)-2-hydroxy]-phenyl}-6-(4-methoxyphenyl)-1,3,5-triazine, dioctylbutylamidotriazone,
2-hydroxy-4-methoxybenzophenone,
2-hydroxy-4-methoxy-4'-methylbenzophenone, 2,2'-dihydroxy-4-methoxybenzophenone,
4-methoxybenzmalonic acid di-2-ethylhexyl ester,
2,4,6-tris-[anilino-(p-carbo-2'-ethyl-1'-hexyloxy)]-1,3,5-triazine,
2,4-bis-[5-1 (dimethylpropyl)benzoxazol-2-yl-(4-phenyl)-imino]-6-(2-ethylhexyl)-imino-1,3,5-triazine,
2,4-bis-{[4-(2-ethyl-hexyloxy)-2-hydroxy]-phenyl}-6-(4-methoxyphenyl)-1,3,5-triazine, and
2-[4,6-bis(2,4-dimethylphenyl)-1,3,5-triazin-2-yl]-5-(octyloxy)phenol.

5. The method of claim 1 wherein said formulation is a cosmetic formulation.

6. The method of claim 1 wherein said formulation is a dermatological formulation.

7. The method of claim 1 wherein said formulation is a pharmaceutical formulation.

8. An oil in water formulation comprising at least one substance of the general formula (I)

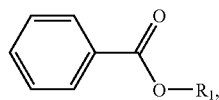

(I)

wherein general formula (I) is isononyl benzoate, and at least one component selected from the group consisting of an emollient, emulsifier, surfactant, thickener, viscosity regulator, stabilizer, UV light protection filter, antioxidant, hydrotropic agent, filler, film-forming agent, pearlescent additive, deodorant active compound, antiperspirant active compound, insect repellent, self-tanning agent, preservative, conditioning agent, perfume, dyestuff, biogenic active compound, care additive, super-oiling agent, and solvent, the proviso that nonyl alcohols obtained by hydrolysis of the at least one substance of general formula (I) contain less than 80 mol % of 3,5,5-trimethylhexanol, wherein the formulation comprises
(a) 0.1-60 percent by weight of the at least one substance of the general formula (I),
(b) 0.1-20 percent by weight of surfactants and/or emulsifiers and/or coemulsifiers,
(c) 0.1-40 percent by weight of further oil substances,
(d) 0-98 percent by weight of water,
wherein the percentages by weight of components (a), (b), (c) and (d) add up to 100 percent by weight to form the oil in water formulation.

9. The formulation of claim 8 wherein that at least one component is at least one UV light protection filter substance, and said at least one substance of formula (I) serves as a solubilizing agent or solvent for said at least one UV light protection filter substance.

10. The formulation of claim 9 wherein the at least one of the UV light protection filter substance is a triazine derivative.

11. The formulation of claim 9 wherein the at least one of the UV light protection filter substances is selected from the group of compounds consisting of
2-cyano-3-phenyl-cinnamic acid 2-ethylhexyl ester,
2,4-bis-{[4-(2-ethyl-hexyloxy)-2-hydroxy]-phenyl}-6-(4-methoxyphenyl)-1,3,5-triazine, dioctylbutylamidotriazone,
2-hydroxy-4-methoxybenzophenone,
2-hydroxy-4-methoxy-4'-methylbenzophenone,
2,2'-dihydroxy-4-methoxybenzophenone,
4-methoxybenzmalonic acid di-2-ethylhexyl ester,
2,4,6-tris-[anilino-(p-carbo-2'-ethyl-1'-hexyloxy)]-1,3,5-triazine,
2,4-bis-[5-1(dimethylpropyl)benzoxazol-2-yl-(4-phenyl)-imino]-6-(2-ethylhexyl)-imino-1,3,5-triazine,
2,4-bis-{[4-(2-ethyl-hexyloxy)-2-hydroxy]-phenyl}-6-(4-methoxyphenyl)-1,3,5-triazine, and
2-[4,6-bis(2,4-dimethylphenyl)-1,3,5-triazin-2-yl]-5-(octyloxy)phenol.

12. The formulation of claim 8 wherein said formulation is a cosmetic formulation.

13. The formulation of claim 8 wherein said formulation is a dermatological formulation.

14. The formulation of claim 8 wherein said formulation is a pharmaceutical formulation.

15. A method for the preparation of an oil in water formulation comprising:
adding at least two substances of the general formula (I)

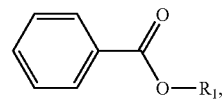

(I)

wherein $R_1$ is an unbranched or branched $C_9$-alkyl radical to at least one component selected from the group consisting of an emollient, emulsifier, surfactant, thickener, viscosity regulator, stabilizer, UV light protection filter, antioxidant, hydrotropic agent, filler, film-forming agent, pearlescent additive, deodorant active compound, antiperspirant active compound, insect repellent, self-tanning agent, preservative, conditioning agent, perfume, dyestuff, biogenic active compound, care additive, super-oiling agent, and solvent, with the proviso that nonyl alcohols obtained by hydrolysis of at least one substance of general formula (I) contain less than 80 mol % of 3,5,5-trimethylhexanol, to form the oil in water formulation.

16. The method of claim 15 wherein the at least one component is at least one UV light protection filter substance, and said at least two substances of formula (I) serve as solubilizing agents or solvents for said at least one UV light protection filter substance.

17. The method of claim 16 wherein the at least one UV light protection filter substance is a triazine derivative.

18. The method of claim 16 wherein the at least one UV light protection filter substance is selected from the group of compounds consisting of
2-cyano-3-phenyl-cinnamic acid 2-ethylhexyl ester,
2,4-bis-{[4-(2-ethyl-hexyloxy)-2-hydroxy]-phenyl}-6-(4-methoxyphenyl)-1,3,5-triazine, dioctylbutylamidotriazone,
2-hydroxy-4-methoxybenzophenone,
2-hydroxy-4-methoxy-4'-methylbenzophenone,
2,2'-dihydroxy-4-methoxybenzophenone,
4-methoxybenzmalonic acid di-2-ethylhexyl ester,
2,4,6-tris-[anilino-(p-carbo-2'-ethyl-1'-hexyloxy)]-1,3,5-triazine,
2,4-bis-[5-1(dimethylpropyl)benzoxazol-2-yl-(4-phenyl)-imino]-6-(2-ethylhexyl)-imino-1,3,5-triazine,
2,4-bis-{[4-(2-ethyl-hexyloxy)-2-hydroxy]-phenyl}-6-(4-methoxyphenyl)-1,3,5-triazine, and
2-[4,6-bis(2,4-dimethylphenyl)-1,3,5-triazin-2-yl]-5-(octyloxy)phenol.

19. The method of claim 15 wherein said formulation is a cosmetic formulation.

20. The method of claim 15 wherein said formulation is a dermatological formulation.

21. The method of claim 15 wherein said formulation is a pharmaceutical formulation.

22. An oil in water formulation comprising at least two substances of the general formula (I)

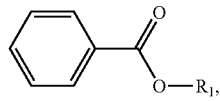

wherein $R_1$ is an unbranched or branched $C_9$-alkyl radical, and at least one component selected from the group consisting of an emollient, emulsifier, surfactant, thickener, viscosity regulator, stabilizer, UV light protection filter, antioxidant, hydrotropic agent, filler, film-forming agent, pearlescent additive, deodorant active compound, antiperspirant active compound, insect repellent, self-tanning agent, preservative, conditioning agent, perfume, dyestuff, biogenic active compound, care additive, super-oiling agent, and solvent, the proviso that nonyl alcohols obtained by hydrolysis of at least one substance of general formula (I) contain less than 80 mol % of 3,5,5-trimethylhexanol to form the oil in water formulation.

23. The formulation of claim 22 including
(a) 0.1-60 percent by weight of the at least two substances of the general formula (I),
(b) 0.1-20 percent by weight of surfactants and/or emulsifiers and/or coemulsifiers,
(c) 0.1-40 percent by weight of further oil substances,
(d) 0-98 percent by weight of water,
wherein the percentages by weight of components (a), (b), (c) and (d) add up to 100 percent by weight.

24. The formulation of claim 22 wherein the at least one component is at least one UV light protection filter substance, and said at least two substances of formula (I) serve as solubilizing agents or solvents for said at least one UV light protection filter substance.

25. The formulation of claim 24 wherein the at least one UV light protection filter substance is a triazine derivative.

26. The formulation of claim 24 wherein the at least one UV light protection filter substance is selected from the group of compounds consisting of
2-cyano-3-phenyl-cinnamic acid 2-ethylhexyl ester,
2,4-bis-{[4-(2-ethyl-hexyloxy)-2-hydroxy]-phenyl}-6-(4-methoxyphenyl)-1,3,5-triazine, dioctylbutylamidotriazone,
2-hydroxy-4-methoxybenzophenone,
2-hydroxy-4-methoxy-4'-methylbenzophenone,
2,2'-dihydroxy-4-methoxybenzophenone,
4-methoxybenzmalonic acid di-2-ethylhexyl ester,
2,4,6-tris-[anilino-(p-carbo-2'-ethyl-1'-hexyloxy)]-1,3,5-triazine,
2,4-bis-[5-1(dimethylpropyl)benzoxazol-2-yl-(4-phenyl)-imino]-6-(2-ethylhexyl)-imino-1,3,5-triazine,
2,4-bis-{[4-(2-ethyl-hexyloxy)-2-hydroxy]-phenyl}-6-(4-methoxyphenyl)-1,3,5-triazine, and
2-[4,6-bis(2,4-dimethylphenyl)-1,3,5-triazin-2-yl]-5-(octyloxy)phenol.

27. The formulation of claim 24 wherein said formulation is a cosmetic formulation.

28. The formulation of claim 24 wherein said formulation is a dermatological formulation.

29. The formulation of claim 24 wherein said formulation is a pharmaceutical formulation.

* * * * *